(12) United States Patent
Marshall

(10) Patent No.: US 8,304,217 B2
(45) Date of Patent: Nov. 6, 2012

(54) STABILIZED DIHYDROLIPOIC ACID AND METHOD OF PRODUCING SAME

(75) Inventor: Robert J. Marshall, Round Rock, TX (US)

(73) Assignee: Premier Research Labs, LP, Austin, TX (US)

( * ) Notice: Subject to any disclaimer, the term of this patent is extended or adjusted under 35 U.S.C. 154(b) by 211 days.

(21) Appl. No.: 10/722,777

(22) Filed: Nov. 26, 2003

(65) Prior Publication Data

US 2005/0112111 A1   May 26, 2005

(51) Int. Cl.
C12P 7/40 (2006.01)
C12P 1/00 (2006.01)

(52) U.S. Cl. .......... 435/136; 435/41
(58) Field of Classification Search .......... 435/41, 435/136
See application file for complete search history.

(56) References Cited

U.S. PATENT DOCUMENTS

| | | | |
|---|---|---|---|
| 3,037,016 A | | 5/1962 | Barker |
| 4,245,048 A | | 1/1981 | Hata et al. |
| 4,769,329 A | | 9/1988 | Cooper et al. |
| 6,080,401 A | * | 6/2000 | Reddy et al. .......... 424/93.3 |
| 6,368,617 B1 | * | 4/2002 | Hastings et al. .......... 424/439 |
| 6,806,069 B2 | | 10/2004 | Chokshi |
| 6,867,024 B2 | | 3/2005 | Chokshi |
| 2003/0095959 A1 | | 5/2003 | Mayne |

FOREIGN PATENT DOCUMENTS

| | | | |
|---|---|---|---|
| DE | 19730538 | * | 10/1999 |
| EP | 1273664 | | 1/2003 |

OTHER PUBLICATIONS

R. Hermann et al. "Enantioselective pharmacokinetics and bioavailability of different racemic c-lipoic acid formulations in healthy volunteers" European Journal of Pharmaceutical Sciences. 4 (1996) 167-174.*
A. Mercenier et al. "Probiotics as Biotherapeutic Agents: Present Knowledge and Future Prospects" Current Pharmaceutical Design, 2003, 9, 175-191.*
Colum Dunne et al. "Probiotics: from myth to reality. Demonstration of functionality in animal models of disease and in human clinical trials" Antonie van Leeuwenhoek 76: 279-292, 1999.*
Pyruvate Dehydrogenase & Krebs Cycle from http://www.rpi.edu/dept/bcbp/molbiochem/MBWeb/mb1/part2/krebs.htm,copyright 1998.*
Lester J. Reed "A Trail of Research from Lipoic Acid to alpha-Keto Acid Dehydrogenase Complexes" The Journal of Biological Chemistry vol. 276, No. 42, Issue of Oct. 19, pp. 38329-38336, 2001.*
Machine Translation for the Description and Abstract of DE19730538 provided by the EPO, accessed Jan. 26, 2009, 11pgs.*
Biewenga et al. "The Pharmacology of the Antioxidant Lipoic Acid" Gen. Pharmac. vol. 29, No. 3, pp. 315-331, 1997.*
Human Translation of DE 19730538, by Schriber Translations, 39 pages, Feb. 2010.*
Lykkesfeldt et al. "Age-associated decline in ascorbic acid concentration, recycling, and biosynthesis in rat hepatocytes-reversal with (R)-a-lipoic acid supplementation" FASEB J. 12, 1183-1189 (1998).*
Packer et al. "Molecular Aspects of Lipoic Acid in the Prevention of Diabetes Complications" Nutrition 2001;17:888-895.*
E.M. Lansford, "Reversal by Ribonucleosides of Bacterial Growth Inhibition Caused by Alcohol," The Journal of Biological Chemistry, 1960, pp. 3551-3554, vol. 235, No. 12, American Society for Biochemistry and Molecular Biology, U.S.
G.R. Gibson, "Colonic Microbiota, Nutrition and Health," 1999, p. 44, Kluwer Academic Publishers, Dordrecht, Netherlands.
R. Meganathan, "Ubiquinone biosynthesis in microorganisms," FEMS Microbiology Letters, 2001, pp. 131-139, vol. 203, No. 2, Blackwell Publishing Ltd., England.
M. Kawamukai, "Biosynthesis, Bioproduction and Novel Roles of Ubiquinone," Journal of Bioscience and Bioengineering, 2002, pp. 511-517, vol. 94, No. 6, Society for Bioscience and Bioengineering, Japan.
J.L. Quiles, "Curcuma longa Extract Supplementation Reduces Oxidative Stress and Attenuates Aortic Fatty Streak Development in Rabbits," Arteriosclerosis, Thrombosis, and Vascular Biology, 2002, pp. 1225-1231, vol. 22, No. 7, Lippincott Williams & Wilkins, U.S.
R.S. Jackson, "Wine Science: Principles, Practice, Perception (2nd ed.)" Apr. 2000, p. 338, Academic Press, U.S.
Dr. Robert J. Marshall: DHLA-Dihydrolipoic Acid, *Literature Search Services*, Nov. 21, 2003, 3 pgs.

* cited by examiner

*Primary Examiner* — Jon P Weber
*Assistant Examiner* — Thane Underdahl
(74) *Attorney, Agent, or Firm* — Amin Talati, LLC; Janine A. Moderson; Jonathan J. Krit

(57) ABSTRACT

A stabilized dihydrolipoic acid (DHLA) compound is provided. The stabilized DHLA is derived from a microbiological culture media including at least one live probiotic organism, R-lipoic acid and at least one nutritive agent. The stabilized DHLA may be prepared by dispersing the microbiological media in distilled water to form a broth, incubating the broth at a predetermined temperature for a select period of time to induce probiotic activity, adding organic ethanol to the broth to halt the probiotic activity, and separating the derived stabilized DHLA from the broth.

12 Claims, No Drawings

STABILIZED DIHYDROLIPOIC ACID AND METHOD OF PRODUCING SAME

FIELD OF INVENTION

The present invention relates to a beneficial compound for use in a medicament and/or a nutritional supplement. More particularly the present invention relates to a stabilized dihydrolipoic acid (DHLA) compound derived from a once living source and a method of producing stabilized DHLA from a microbiological culture media.

BACKGROUND OF THE INVENTION

Reactive oxygen species (ROS) are byproducts of the normal metabolism of living organisms. ROS include oxygen-derived free radicals and non-radical derivatives that can cause oxidative damage to biological structures. ROS have also been shown to play a role in the aging process and a number of pathological syndromes such as, for example, diabetes. However, oxidative damage caused by ROS can be reduced or prevented through a number of mechanisms such as, for example, the use of low molecular weight antioxidants that can react directly with ROS in the body.

Such low molecular weight antioxidants include lipoic acid, dihydrolipoic acid and other lipoic acid derivatives. Over the last several years these particular antioxidants have been intensively studied as potentially useful therapeutic agents. Results from model and clinical studies have demonstrated that both lipoic acid and dihydrolipoic acid (DHLA) are capable of scavenging ROS such as, for example, singlet oxygen, hypochlorous acid and the trichloromethylperoxyl radical, and hydroxyl radicals. In addition, both compounds may chelate redox-active transition metal ions such as, for example, copper and iron. Under normal circumstances, copper and iron are typically complexed with other proteins. But, under some conditions of trauma, such transition metals can be released and act as catalyzing agents in oxidative processes that can cause cellular damage.

Lipoic acid or alpha-lipoic acid (ALA), and DHLA are naturally synthesized by living organisms at a cellular level. Normally, DHLA is formed in the cells. Cells tend to absorb ALA, reduce it to DHLA and then secrete the DHLA into the blood stream. Once in the blood stream, DHLA can react with an oxidizing agent such as, for example, oxidized vitamin C thereby scavenging oxygen from and regenerating the vitamin C, and form ALA that can be reabsorbed by the cells. However, cells generally only produce an amount of DHLA sufficient for metabolic function. Additional or supplemental amounts of lipoic acid or DHLA must generally be derived from external sources such as dietary intake and/or nutritional supplements.

Until recently, naturally occurring DHLA could only be obtained indirectly through consuming ALA, which in turn, was converted by the body into small amounts of DHLA. However, this process does not deliver a significant or reliable supply of DHLA. Thus, ALA and DHLA for use in dietary supplements and medicaments have typically been derived from synthetic sources.

Several research studies show the benefits from the use of alpha-lipoic acid (ALA). Unfortunately, most of these research studies have used a synthetic form that contains equal amounts of the R- and the S-racemic forms of lipoic acid. The S-form occurs only in synthetic source ALA and has a negative, pro-inflammatory effect on body tissues. Thus, DHLA derived from such synthetic ALA exhibits both desirable antioxidant properties and undesirable pro-oxidant properties.

Thus, there is a need and a demand for a beneficial compound such as a stabilized dihydrolipoic acid (DHLA) compound that can be derived from a natural source. In particular, there is a need and a demand for a DHLA compound derived from a once-living source that is stable and, in long term use, capable of preventing and/or repairing oxidative damage to tissue, DNA and/or other important chemicals in the body such as, for example, vitamins C and E. There is a further need and a demand for a microbiological culture media and method for preparing a stabilized DHLA compound for use in a medicament or a nutritional supplement.

SUMMARY OF THE INVENTION

A general object of the invention is to provide a beneficial compound that is derived from a natural source for use in a medicament and/or a nutritional supplement.

A particular objective of the invention is to provide a stabilized dihydrolipoic acid (DHLA) compound derived from a "once living" source that is capable of imparting significant, long-term DNA and cellular benefits.

A more specific objective of this invention is to overcome one or more of the problems described above.

The general object of the invention can be attained, at least in part, through a beneficial compound for use in a medicament or a nutritional supplement derived by preparing a microbiological culture including at least one live probiotic organism and at least one nutraceutical or nutritive agent, incubating the microbiological culture to initiate probiotic activity, harvesting a waste byproduct of the probiotic activity, and separating the beneficial compound from the waste byproduct. A particular object of the invention can be attained, at least in part, through providing a stabilized DHLA compound derived from a microbiological culture media including at least one live probiotic organism, R-lipoic acid, and at least one nutraceutical or nutritive agent.

The prior art has generally failed to provide a DHLA compound that is as effective as desired in satisfying one or more of the above-identified performance criteria. Furthermore, the prior art has generally failed to identify a method for producing a stabilized DHLA compound. Additionally, the prior art has generally failed to provide a method for deriving a beneficial compound from a once-living source such as by feeding a probiotic organism a nutraceutical or nutritive agent and separating the beneficial compound from the waste byproduct. Moreover, the prior art has generally failed to identify a microbiological culture media that can be utilized to produce a stabilized DHLA compound.

The invention further comprehends a microbiological culture media for producing a stabilized dihydrolipoic acid compound including:
- about 40 composition weight percent of a paste including at least one live probiotic organism;
- about 20 composition weight percent of R-lipoic acid; and
- about 40 composition weight percent turmeric rhizome (*curcuma longa*) nutritive agent.

The invention still further comprehends a process for preparing a stabilized dihydrolipoic acid (DHLA) compound including dispersing a microbiological culture media including at least one live probiotic organism, R-lipoic acid and at least one nutritive agent in distilled water to form a broth, incubating the broth at a predetermined temperature for a select period of time to induce probiotic activity; adding organic ethanol to halt the probiotic activity, and separating the stabilized DHLA from the broth.

Other objects and advantages will be apparent to those skilled in the art from the following detailed description taken in conjunction with the appended claims.

DETAILED DESCRIPTION OF THE INVENTION

The present invention provides a beneficial compound for use in a medicament or a nutritional supplement that can be derived from a natural source such as by feeding a probiotic organism a nutraceutical or nutritive agent, harvesting the waste byproducts and separating the beneficial compound from the waste byproduct. The present invention further provides a stabilized dihydrolipoic acid (DHLA) compound derived from a once living source for use in a medicament or a nutritional supplement. The present invention also provides a microbiological culture media and process for preparing a stabilized DHLA compound.

As noted above, DHLA is typically produced within the body through the redox conversion of lipoic acid or alpha-lipoic acid (ALA) during normal metabolic activity. However, the body generally only produces an amount of DHLA sufficient to assist in metabolic function. However, DHLA has been shown, at least in part, to be an effective antioxidant and chelating agent that can be utilized to scavenge reactive oxygen species (ROS) such as, for example, singlet oxygen, that can contribute to a number of degradative pathological syndromes such as diabetes, glaucoma, atherosclerosis, and other neuropathies. DHLA has also been found, at least in part, to be effective to prevent or repair oxidative damage in cells and to regenerate certain important nutrients in the body such as, for example, vitamins C and E. However, most DHLA is derived indirectly from synthetic sources of ALA. As a result, it is believed that such synthetically derived DHLA is not stable over time and may contribute to early cell death and other degenerative cellular processes. Thus, it is believed that DHLA derived from a once living source is stable and, over time, is capable of sustaining cellular DNA within the body.

In accordance with certain preferred embodiments of the invention, stabilized dihydrolipoic acid (DHLA) for use in a medicament or nutritional supplement is derived from a once living source. In particular, the stabilized DHLA compound can be derived from a microbiological culture media including at least one live probiotic organism, R-lipoic acid, and at least one nutraceutical or nutritive agent.

While various live probiotic organisms can be included in the microbiological culture media of the invention, in accordance with certain preferred embodiments, the at least one probiotic organism can be selected from Lactobacillus species, *Bifidobacterium* species, *Enterococcus* species, generally accepted as safe (GRAS) *Streptococcus thermophilus*, and combinations thereof. In accordance with another preferred embodiment of the invention, the microbiological culture media can include at least one live probiotic organism selected from *Lactobacillus* species and at least one live probiotic organism selected from *Bifidobacterium* species.

Examples of suitable *Lactobacillus* species include, but are not limited to, *L. acidophilus, L. paracasei, L. fermentum, L. rhamnosus, L. johnsonii, L. plantarum, L. reuteri, L. salivarius, L. brevis, L. bulgaricus, L. helveticus, L. grasseri, L. casei, L. lactis*, and combinations thereof.

Examples of suitable *Bifidobacterium* species include, but are not limited to, *B. bifidum, B. breve, B. infantis, B. longum, B. lactis* and combinations thereof.

Examples of suitable *Enteroococcus* species include, but are not limited to, *E. faceum, E. faecalis*, and combinations thereof.

As discussed above, synthetic sources of alpha-lipoic acid (ALA) generally include, in equal amounts, R-lipoic acid and S-lipoic acid. However, it has been discovered, that DHLA derived from ALA containing S-lipoic acid possesses pro-inflammatory properties which results in the formation of undesirable compounds and may detract from the function of DHLA. In practice, therefore, R-lipoic acid is utilized in the microbiological culture media.

While various nutraceuticals or nutritive agents can be utilized in the microbiological culture media of the invention, suitable nutraceuticals or nutritive agents should contribute to the production of DHLA as well as contribute to the stability of the microbiological media. In accordance with certain preferred embodiments, the nutraceutical or nutritive agent can be turmeric rhizome (*curcuma longa*).

In practice, the microbiological culture media of the present invention can include about 40 composition weight percent of a paste including at least one live probiotic organism, about 20 composition weight percent R-lipoic acid, and about 40 composition weight percent of turmeric rhizome (*curcuma longa*) nutritive agent.

In accordance with certain preferred embodiments of the invention, a beneficial compound for use in a medicament or a nutritional supplement may be derived by preparing a microbiological culture including at least one live probiotic organism and at least one nutraceutical or nutritive agent, incubating the culture to initiate probiotic activity, harvesting a waste byproduct of the probiotic activity, and separating a beneficial compound from the waste byproduct.

The stabilized dihydroplipoic acid (DHLA) of the present invention may be prepared by dispersing a microbiological culture media including at least one live probiotic organism, R-lipoic acid and at least one nutritive agent in distilled water to form a broth. The broth is then incubated at a predetermined temperature such as, for example, about 35° C. to about 40° C., for a select period of time such as, for example, about 72 to about 168 hours (i.e. about 3 to about 7 days) to induce probiotic activity. At the end of the incubation period, organic ethanol is added to the broth to halt the probiotic activity and preserve the synthesized compounds. Thereafter, the naturally derived DHLA can be separated from the broth and used to prepare a medicament or nutritional supplement.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A liquid composition made by a method comprising the steps:
   incubating at 35° C. to 40° C. a solution comprising:
      at least one species of live, dihydrolipoic acid producing microorganisms;
      about 20 wt % R-lipoic acid; and
      at least 40 wt % turmeric rhizome (curcuma longa);
   halting the incubation by adding ethanol in an amount sufficient to render the microorganism once-living;
   wherein the resulting in situ produced dihydrolipoic acid in the composition has an extended half-life in an aqueous solution.

2. The liquid composition according to claim 1, wherein the at least one species of microorganisms is selected from the group consisting of *Lactobacillus* species, *Bifidobacterium* species, *Enterococcus* species, *Streptococcus thermophilus*, and combinations thereof.

3. The liquid composition according to claim 2, wherein the at least one species of microorganisms comprises a *Lactobacillus* species.

4. The liquid composition according to claim 3, wherein the *Lactobacilus* species is selected from the group consisting of *L. acidiophilus, L. paracasei, L. fermentum, L. rhamnosus, L. johnsonii, L. plantarum, L. reuteri, L. salivarius, L. brevis, L. bulgaricus, L. helveticus, L. grasseri, L. casei, L. lactis*, and combinations thereof.

5. The liquid composition according to claim 2, wherein the at least one species of microorganisms comprises a *Bifidobacterium* species.

6. The liquid composition according to claim 5, wherein the *Bifidobacterium* species is selected from the group consisting of *B. bifidum, B. breve, B infantis, B. longum, B. lactis*, and combinations thereof.

7. The liquid composition according to claim 2, wherein the at least one species of microorganisms comprises an *Enterococcus* species.

8. The liquid composition according to claim 7, wherein the *Enterococcus* species is selected from the group consisting of *E. faecium, E. faecalis*, and combinations thereof.

9. The liquid composition according to claim 1, wherein the composition is used in a medicament or nutritional supplement.

10. A liquid composition made by a method comprising the steps:
    incubating at 35° C. to 40° C. a solution comprising:
        at least one species of live, dihydrolipoic acid-producing microorganisms selected from the group consisting of *Lactobacillus* species, *Bifidobacterium* species, *Enterococcus* species, *Streptococcus thermophilus*, and combinations thereof;
        about 20 wt % R-lipoic acid;
        an aqueous nutrient medium; and
        at least 40 wt % turmeric rhizome (curcuma longa);
    halting the incubation by adding ethanol in an amount sufficient to render the microorganism once-living;
    wherein the resulting in situ produced dihydrolipoic acid in the composition has an extended half-life in an aqueous solution.

11. A medicament or nutritional supplement made by a method comprising the steps:
    incubating at 35° C. to 40° C. a solution comprising:
        at least one species of live, dihydrolipoic acid producing microorganisms
        about 20 wt % R-lipoic acid; and
        at least 40 wt % turmeric rhizome (curcuma longa);
    halting the incubation by adding ethanol in an amount sufficient to render the microorganism once-living;
    wherein the resulting in situ produced DHLA in the composition has an extended half-life in an aqueous solution.

12. The medicament according to claim 11, wherein the at least one species of once-living microorganisms is selected from the group consisting of *Lactobacillus* species, *Bifidobacterium* species, *Enterococcus* species, *Streptococcus thermophilus*, and combinations thereof.

* * * * *